United States Patent
Mukherjee et al.

(10) Patent No.: US 6,610,741 B1
(45) Date of Patent: Aug. 26, 2003

(54) SKIN COSMETIC COMPOSITIONS CONTAINING A WEAK CARBOXYLIC ACID AND RANDOM COPOLYMERS OF ETHYLENE OXIDES AND PROPYLENE OXIDES

(75) Inventors: Surajit Mukherjee, Ridgewood, NJ (US); Donald Rick, Dumont, NJ (US); Stephan Samuel Habif, Demarest, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 2 days.

(21) Appl. No.: 09/640,028

(22) Filed: Aug. 16, 2000

Related U.S. Application Data

(60) Provisional application No. 60/150,111, filed on Aug. 20, 1999.

(51) Int. Cl.[7] .................. A61K 31/19; A61K 47/34; A01N 37/00; A01N 25/00
(52) U.S. Cl. .................. 514/557; 514/558; 514/772; 514/772.3; 514/828; 514/844
(58) Field of Search .................. 424/401, 65, 78.03, 424/78.05; 514/557, 558, 772.3, 784, 828, 844–848, 858–865, 873, 938, 943–947, 975

(56) References Cited

U.S. PATENT DOCUMENTS

| | | | |
|---|---|---|---|
| 4,105,783 A | | 8/1978 | Yu et al. .................. 424/283 |
| 4,511,554 A | * | 4/1985 | Geria et al. .................. 424/65 |
| 4,514,325 A | | 4/1985 | Russo et al. .................. 252/557 |
| 4,670,168 A | * | 6/1987 | Laemmle et al. ........... 508/512 |
| 4,970,220 A | | 11/1990 | Chaussee .................... 514/358 |
| 5,616,335 A | | 4/1997 | Nicolle et al. .............. 424/405 |
| 5,683,705 A | * | 11/1997 | Maes et al. .................. 424/401 |
| 5,690,923 A | | 11/1997 | DeVringer et al. ...... 424/78.02 |
| 5,919,830 A | | 7/1999 | Gopalkrishnan et al. . 514/772.1 |
| 6,280,758 B1 | * | 8/2001 | Warren et al. .............. 424/404 |

FOREIGN PATENT DOCUMENTS

| | | |
|---|---|---|
| WO | 92/19216 | 11/1992 |
| WO | 96/15761 | 5/1996 |

OTHER PUBLICATIONS

Johansson et al, "Experimental and Theoretical Study of Phase Separation in Aqueous Solutions of Clouding Polymers and Carboxylic Acids", Macromolecules, 1993, 26, pp. 4478–4483.*
PCT International Search Report in a PCT application PCT/EP 00/07302, Jan. 22, 2001.
Derwent Abstract of JP 61 180712—published Aug. 13, 1986/.
Derwent Abstract of JP 08 231381—published Sep. 10, 1996.
Sah et al. Journal of Cosmetic Science, vol. 49, 257–273 (Jul./Aug. 1998).

* cited by examiner

Primary Examiner—Sreeni Padmanabhan
Assistant Examiner—Michael A. Willis
(74) Attorney, Agent, or Firm—Ellen Plotkin

(57) ABSTRACT

Cosmetic skin compositions containing a weak carboxylic acid and a random copolymer of ethylene oxide and propylene oxide. The copolymer reduces skin irritation that is sometimes caused by the weak acid active without reducing delivery of weak acids to skin tissues.

3 Claims, No Drawings

SKIN COSMETIC COMPOSITIONS CONTAINING A WEAK CARBOXYLIC ACID AND RANDOM COPOLYMERS OF ETHYLENE OXIDES AND PROPYLENE OXIDES

This application claims the benefit of U.S. provisional application Ser. No. 60/150,111 filed Aug. 20, 1999.

FIELD OF THE INVENTION

Cosmetic compositions for human skin containing a weak carboxylic acid and a random copolymer of ethylene and propylene oxides.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin.

Some ingredients used in topical products are potentially irritating, especially to people with "sensitive skin." Such irritation is commonly perceived as sting or burning.

As an example, hydroxy acids and several other weak carboxylic acids have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. For aesthetic reasons, these actives are most often delivered as oil-in-water emulsions. Practically, the final composition pH should be higher than 3 in order to prevent deleterious effects to skin tissues and unacceptable levels of irritation. Water soluble weak acids when delivered from an oil-in-water emulsion at acidic pH often induce high levels of sting. The sting occurs immediately after application, reaches a maximum intensity usually by 5–8 minutes after application and then begins to reduce in intensity.

The irritation can be ameliorated by lowering the amount of an active ingredient in the composition or by reducing the active's penetration through the skin. A serious drawback of both approaches is that the efficacy of the active is impaired. The weak acid related irritation can be reduced by raising the composition's pH but this method yields reduced efficacy due to a decreased acid penetration through the skin. It is desirable to reduce or eliminate the irritation potential of weak acids while maintaining their efficacy.

The need exists, therefore, for a composition and method that prevents or reduces the skin irritation.

One approach to lower the sting is to formulate the acid with a strong alkali metal base. Yu et al. (U.S. Pat. No. 4,105,783) suggested the use of ammonium hydroxide or an organic base. Unfortunately, this method raises the pH of the composition and reduces the ability of the weak acid to penetrate the skin, thus lowering its efficacy (see Sah et al. in *J. Cosmet. Sci*. 49, 257–273, 1998).

A clear need exists for a cosmetic composition with a weak acid that reduces sting but does not reduce dermal delivery.

The random copolymers of ethylene oxide (EO) and propylene oxide (PO) have not been used in cosmetics. They are commonly used industrial lubricants for the metalworking industry such as described by Russo et al. in U.S. Pat. No. 4,514,325. The block copolymers (e.g. BASF Pluronic series) have been used in the cosmetic industry. But the random copolymers employed in the present invention are different structurally and have different properties from the block copolymers of EO and PO.

SUMMARY OF THE INVENTION

The present invention includes a skin cosmetic composition comprising:

(i) from about 0.1 to about 20 wt. % of a random copolymer of ethylene oxide and propylene oxide having a number average molecular weight of at least about 1,000D and containing less than 70% propylene oxide units by weight of the copolymer;

(ii) from about 0.01 to about 20 wt. % of a weak carboxylic acid having pKa of above about 2; and (iii) a cosmetically acceptable vehicle.

The invention provides a method for reducing skin irritation that may be caused by the topical application of a weak carboxylic acid, the method comprising topically applying random EO/PO copolymer in a cosmetically acceptable vehicle.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition, unless otherwise specified.

The term "skin" as used herein includes the skin on the face, neck, chest, back, arms, armpits, hands and scalp.

The terms "irritation," "sting," and "burn," "inflammation,", and "redness" as used herein are synonymous and are used interchangeably.

The molecular weight is expressed in Dalton (D). The numerical terms followed by letters "KD" denote molecular weight of a compound, to be read as the numerical term ×1,000 (e.g. 10 KD means molecular weight of 10,000 D).

EO/PO Copolymer

The EO/PO copolymers used in this invention are linear random copolymers of ethylene oxides (EO) and propylene oxides (PO). An example of such a copolymer is UCON 50-HB-5100 from Union Carbide which is a 50/50 EO/PO copolymer with a number average molecular weight of 3930 D. The ratio of EO to PO must result in the copolymer remaining substantially water soluble, so that the copolymer remains effective at preventing the sting caused by the weak acid. As the ratio of PO increases above 50%, the molecule becomes less water soluble. At the PO content of 70% or more, the copolymer is water insoluble and is not suitable for use in the present invention. Union Carbide supplies EO/PO random copolymers in 3 main groups: LB fluids contain only oxypropylene groups, are water insoluble, and are not suitable for use in the inventive compositions, 50-HB fluids which contain equal amounts by weight of oxyethylene and oxypropylene groups, and 75-H fluids which contain 75 weight percent oxyethylene and 25 weight percent oxypropylene groups. These fluids are available with number average molecular weights from about 250 D to about 12,000 D. The copolymers suitable for use in the present invention have the molecular weight of at least about 1,000 D. The preferred molecular weight range is from about 1,000 D to about 12,000 D, in order to optimize the efficacy of the copolymer.

Weak Carboxylic Acid

A weak carboxylic acid suitable for use in the inventive compositions is an acid with dissociation constant, pKa, of above about 2. Preferably, the pKa is above about 3, most preferably in the range of from about 3 to about 5.

The concept of pKa

An acid is a species having a tendency to lose a proton, while a base is a species having a tendency to accept a proton. Hence for every acid, HA, there is a conjugate base $A^-$:

$$HA \rightleftharpoons H^+ + A^-$$

Thus, lactic acid-lactate ion is an example of a conjugate acid-base pair.

Acids so defined can only manifest their properties by reacting with bases. In aqueous solutions, acids react with water, the latter acting as a base $$HA + H_2O \rightleftharpoons H_3O^+ + A^-$$

Quantitatively, the acid strength of HA, relative to the base strength of water is given by the equilibrium constant expression by the equation $$K=[H_3O^+][A^-]/[H_2O][HA]$$

where parentheses denote molar concentrations.

As almost all measurements are made in dilute aqueous solution, the concentration of water remains essentially constant and its activity can be taken as unity. Letting $H^+$ represent the solvated proton, we have $$K_a=[H^+][A^-]/[HA]$$

where $K_a$ is the acidic dissociation (or ionization) constant. This equation can be written in the form $$pK_a = pH + \log [HA]/[A^-]$$

where $pK_a$ is the negative logarithm of $K_a$, and is equal to the pH at which the concentrations of HA and $A^-$ are equal.

$pK_a$ for alpha hydroxy acids are generally between 2–4, for monocarboxylic acids between 3–5, for alpha amino acids between 2–3; for salicylic acid it is 3.0.

The $pK_a$ of a weak water-soluble acid is obtained by titrating it with a strong base such as sodium hydroxide (NaOH). The intercept at the midpoint of the titration, ie. the point at which 0.5 molar equivalents of base have been added, is numerically equal to the pKa of the acid.

A procedure for determining pKa for a known weak acid is as follows:

Materials

Sample of pure acid for which pKa is to be determined; $CO_2$-free deionized distilled water (prepared by boiling deionized distilled water for 5 minutes); Commercial 0.1N NaOH volumetric standard, certified to 0.1005–0.0995 N, eg. Fisher Scientific SS276 ; 100-ml calibrated glass burette; 125-ml Erlenmeyer flask pH meter, eg. Corning Model 140 with standard combination electrode for pH; pH buffers, pH 4.00, 7.00, and 10.00, certified to ±0.01 pH unit at 25, eg. Fisher Scientific SB101, SB107, and SB115 magnetic stirrer Method Be sure all glassware and equipment is clean. Acid-wash if necessary. Prepare at least 50 ml of a 0.1 Normal solution of the acid for which the pKa is to be determined in CO2-free distilled water. Avoid introducing $CO_2$ to the solution by avoiding excessive shaking. Cap the final solution until use. Calibrate the pH meter using three buffers, pH 7.00, 3.00, and 10.00, according to pH meter manufacturer's instructions. Rinse electrode with distilled water between samples. Fill burette with 0.1 N NaOH standard solution. Add 50.0 ml of 0.1 N acid solution to 125-ml Erlenmeyer. Add stir bar to Erlenmeyer.

Insert pH electrode into acid solution. Position and secure electrode so that it does not interfere with stir bar. Record initial pH. Begin gentle stirring such that pH reading is not affected. Position burette over flask to allow incremental addition of 0.1 N standard NaOH to 0.1 N acid solution. Verify initial pH and begin incremental addition of base. Record the volumes of base added and resulting pH readings. Aim to record pH changes of 0.2 to 0.3 units or volume increases of about 5 ml, whichever comes first. Continue incremental additions until at least 60 ml of base have been added and the steep change in pH levels off.

Plot the data with the volume of base as the x-axis and pH as the y-axis. Plot the points observed and draw a smooth line through them. Determine the volume of base added to obtain the equivalence point, i.e. the volume at which one normal-equivalent of base has been added and the acid has been completely neutralized: When the steep portion of the curve is vertical, the equivalence point volume corresponds to the volume of base at the vertical portion of the curve. If the steep portion of the curve is not vertical, the equivalence point can be obtained by locating the volumes of the base at the two end points that bracket the steep change in pH. The mean of the two volumes is the equivalence point.

To determine the pKa, first locate the midpoint of the titration by halving (i.e. ÷2) the volume of base at equivalence point. The midpoint of the titration is the point at which 0.5 normal-equivalents of base have been added, and the acid has been one-half (50%) neutralized. The pH corresponding to the midpoint of the titration is the $pK_a$ of the acid. This is the pH at which 50% of the acid has been neutralized, that is, and the molecule exists 50% in the non-ionized form and 50% as the anion.

Examples of suitable weak carboxylic acids include but are not limited to: alpha- or beta-hydroxyacids, dicarboxylic acids, tricarboxylic acids, ascorbic acid, oxamic acid and mixtures thereof. Preferred carboxylic acids, due to their anti-aging afficacy, are:

| ACID | pKa |
|---|---|
| glycolic | 3.8 |
| lactic | 3.8 |
| malic | 3.4 |
| beta-hydroxybutyric | 4.7 |
| acetic | 4.75 |
| succinic | 4.2 |
| citric | 3.1 |
| ascorbic | 4.1 |
| salicylic | 3.0 |
| oxamic | 2.4 |
| and mixtures thereof. | |

The amount of weak acid in the inventive composition ranges from 0.01 to 20, preferably from 1 to 15 and most preferably from 2 to 12, by weight of the composition. At concentrations below 2% of the acid, there is minimal stinging and the anti-aging efficacy does not increase significantly above 12%.

It is to be understood that depending on the pH of the composition, the acid may be present as a salt, e.g. ammonium or potassium or sodium salt.

Although the inventive compositions may have any pH in the general range of 2.5 to 10, the inventive compositions are particularly useful when they are at an acidic pH, preferably 3–6 and most preferably at a pH of 3–5, because such compositions, although efficacious, are particularly irritating.

The compositions according to the invention comprise a cosmetically acceptable vehicle to act as a diluant, dispersant or carrier for weak carboxylic acid and the EO/PO copolymer, so as to facilitate their distribution when the composition is applied to the skin.

The vehicle may be aqueous or an emulsion. Water when present will be in amounts which may range from 5 to 99%, preferably from 40 to 90%, optimally between 50 and 85% by weight.

According to the present invention, the vehicle is preferably at least 50 wt. % water, by weight of the vehicle. The inventive compositions are preferably oil-water emulsions, in order to improve dermal delivery of hydroxy acids (See Sah et al. in *J. Cosmet. Sci.* 49, 257–273, 1998). Such improved delivery is frequently accompanied by increased irritation/sting, making the use of PEG in such emulsions particularly critical. In the preferred oil-in-water emulsions according to the present invention, water comprises at least 50 wt. % of the inventive emulsion, most preferably from 50 to 85 wt. %, by weight of the composition.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients and sunscreens.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

The composition according to the invention is intended primarily as a product for topical application to human skin, especially as an agent to improve the appearance of aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging:

The cosmetic skin composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

List of suppliers

| Active Ingredient | Supplier |
|---|---|
| EO/PO copolymers. | Union Carbide |
| Arabinogalactan | Larex, Inc. |
| Glycolic acid | DuPont |
| Lactic acid | Purac America, Inc. |
| Hydrocortisone (water soluble) | Sigma |

EXAMPLE 1

This example measured sting caused by formulations containing glycolic acid.

Procedure for in-vivo sting test: This was a randomized, double blind study where each subject evaluated one test formulation and a control formulation or two test formulations on contralateral nasolabial folds. During the qualification phase, each subject evaluated an 8% glycolic acid test versus a vehicle control (0% glycolic). Subjects with established left/right balanced sensitivity to glycolic acid were qualified. A maximum of 20 qualified subjects (minimum of 15) were utilized in each subsequent test. One paired comparison was made on each testing day, with a minimum of 3 days between sting testing throughout the study. Subjects underwent a 15 second Ivory soap wash regime immediately prior to product testing for enhancing sting response. Any subjects experiencing any stinging/burning on the test sites immediately prior to product application did not have products applied. Study personnel then applied one test formulation and one control or test formulation simultaneously to the appropriate left/right test site, and gently but thoroughly rubbed in. Subjects compared the stinging potential of the two formulations, over a 7.5 minute period using a self-assessment questionnaire.

Sting/Burn Propensity: The degree of stinging/burning felt on the left and right inner cheek and crease of the nose was evaluated using the following scale at the times indicated in Tables below:

0-no stinging/burning; 1-very slight stinging/burning; 2-slight stinging/burning; 3- moderate stinging/burning; 4-moderately high stinging/burning; 5-high stinging/burning; 6-extreme stinging/burning.

Determination of Statistical Significance: At each evaluation time point after baseline, the parametric paired t-test (two-tailed) was performed, to compare the extent of attribute change from baseline between each treatment comprising a paired comparison test, with subject acting as a block in these analyses. (Ref. *Statistical Methods*, Snedecor and Cochran, Iowa State University Press, 7th Edition, 1980, pp. 84–86]). The test can be implemented using the SAS software procedure MEANS with the T and PRT options specified.

Forced choice for stinging/burning: At each evaluation point (0,2.5,5.0 and 7.5 min), the response to the forced choice assessment "Which side of the face has more stinging?" was analysed as follows: the number of subjects choosing treatment A was compared to the number of subjects choosing treatment B using a parametric paired t-test (2-tailed). Statistical significance was determined at $p \leq 0.1$. Results from several paired comparisons using this assessment method are shown (see later) in Tables 1B and 2B.

An oil-in-water emulsion cream (Base Formula A) was prepared:

| FULL CHEMICAL NAME OR CTFA NAME | % ACTIVE LEVEL IN FORMULATION | TRADE NAME AND % ACTIVE AS RECEIVED |
|---|---|---|
| water, DI | 46.54 | |
| disodium EDTA | 0.05 | Sequesterene Na2 |
| magnesium aluminum silicate | 0.6 | Veegum Ultra |
| methyl paraben | 0.15 | Methyl Paraben |
| simethicone | 0.01 | DC Antifoam Emulsion |
| butylene glycol 1,3 | 3.0 | Butylene Glycol 1,3 |
| hydroxyethylcellulose | 0.5 | Natrosol 250HHR |
| glycerine, USP | 2.0 | Glycerine USP |
| xanthan gum | 0.2 | Keltrol 1000 |
| triethanolamine | 1.2 | Triethanolamine 99% |
| stearic acid | 3.0 | Pristerene 4911 |
| propyl paraben NF | 0.1 | Propylparaben NF |
| glyceryl hydrostearate | 1.5 | Naturechem GMHS |
| stearyl alcohol | 1.5 | Lanette 18DEO |
| isostearyl palmitate | 6.0 | Protachem ISP |
| C12–15 alcohols octanoate | 3.0 | Hetester FAO |
| dimethicone | 1.0 | Silicone Fluid 200 (50 cts) |
| cholesterol NF | 0.5 | Cholesterol NF |
| sorbitan stearate | 1.0 | Sorbitan Stearate |
| butylated hydroxytoluene | 0.05 | Embanox BHT |
| tocopheryl acetate | 0.1 | Vitamine E Acetate |
| PEG-100 stearate | 2.0 | MYRJ 59 |
| sodium stearoyl lactylate | 0.5 | Pationic SSL |
| water, DI | q.s. to 99.80 | |

The sting/burn of Base Formula A with or without 8% glycolic acid was tested using the in-vivo sting test. The results that were obtained are summarized in Tables 1A and 1B.

TABLE 1A

Sting/Burn Propensity

| Mean Degree of Stinging/Burning (0–6 Scale) | Base Formula A (pH 7.2) | Base Formula A + 8% Glycolic Acid (pH 3.8) |
|---|---|---|
| Immediately after application | 0.05 | 1.05* |
| 2.5 minutes after Application | 0.25 | 1.85* |
| 5.0 minutes after Application | 0.25 | 2.00* |
| 7.5 minutes after Application | 0.35 | 2.15* |

*p < 0.05

TABLE 1B

Forced Choice for Stinging/Burning: Which side is worse? Results 7.5 minutes after application

| | Base Formula A (pH 7.2) | Base + 8% Glycolic Acid (pH 3.8) |
|---|---|---|
| Number of Subjects Indicating more Discomfort (sting/burn) | 0 | 20 |

*p < 0.05

The sting/burn propensity of glycolic at 8% and 4% level were compared. The results that were obtained are summarized in Table 1C.

TABLE 1C

Sting/Burn Propensity

| Mean Degree of Stinging/Burning (0–6 Scale) | Base Formula A + 4% Glycolic Acid (pH 3.8) | Base Formula A + 8% Glycolic Acid (pH 3.8) |
|---|---|---|
| Immediately after application | 0.45 | 1.35* |
| 2.5 minutes after Application | 0.60 | 1.75* |
| 5.0 minutes after Application | 0.60 | 1.95* |
| 7.5 minutes after Application | 0.55 | 1.65* |

*p < 0.05

It can be seen from the results in Tables 1A–1C that 8% glycolic acid at pH 3.8 is significantly more stinging than either the base formulation or 4% glycolic acid. Although, sting can be reduced by increasing pH or lowering the active level, such changes in composition significantly affect dermal delivery and, consequently, the efficacy of the active.

EXAMPLE 2

This example measured the effect of UCON 50-HB-5100 on glycolic acid sting at pH 3.8 in Base Formula A. The in-vivo sting test and Base Formula A are described in Example 1.

Base Formula A was prepared without the glycolic acid, base, and EO/PO copolymer. In a separate beaker glycolic acid+base (ammonium hydroxide) and a small level of water from the formulation (no more than 5% is needed)—thus, the original Base Formula A was originally made with 5% less water. The glycolic acid solution was then post added to the Base Formula A during the cool down stage (usually at a temperature of about 45° C.). The EO/PO polymer, UCON 50-HB-5100 was then added to the formulation. The EO/PO polymer is easily post added as it is a liquid which mixes easily into the water phase of the emulsion. The results that were obtained are summarized in Tables 2A and 2B.

TABLE 2A

Sting/Burn propensity

| Mean Degree of Stinging/Burning (0–6 Scale) | Base Formula A + 8% Glycolic + 5% UCON 50-HB-5100 (pH 3.8) | Base Formula A + 8% Glycolic (pH 3.8) |
|---|---|---|
| Immediately after application | 0.38 | 0.63 |
| 2.5 minutes after Application | 0.44 | 1.0* |
| 5.0 minutes after Application | 0.38 | 0.75 |
| 7.5 minutes after Application | 0.31 | 0.63 |

*p < 0.1

TABLE 2B

Forced Choice for Stinging/Burning; Which side is worse? Results 2.5 minutes after application

| | Base Formula A + 8% Glycolic + 5% UCON 50-HB-5100 (pH 3.8) | Base Formula A + 8% Glycolic (pH 3.8) |
|---|---|---|
| Number of Subjects Indicating more Discomfort (sting/burn) | 2 | 9* | p < 0.1

It can be seen from the results in Tables 2A and 2B that UCON 50-HB-5100 significantly reduced the stinging/burning propensity of Base Formula A containing 8% glycolic acid.

COMPARATIVE EXAMPLE 3

This example tested various compounds for their ability to reduce sting. The test procedure and Base Formula A are described in Example 1. UCON 50-HB-100 is random EO/PO copolymer containing 50% EO and 50% PO and having molecular weight of about 200 D. The results that were obtained are summarized in Tables 3A–3C.

TABLE 3A

Hydrocortisone

| Mean Degree of Stinging/ Burning (0–6 Scale) | Base Formula A + 8% Glycotic + 0.1% Hydrocortisone (pH 3.8) | Base Formula A + 8% Glycolic (pH 3.8) |
|---|---|---|
| Immediately after application | 0.94 | 0.76 |
| 2.5 minutes after Application | 0.68 | 0.58 |
| 5.0 minutes after Application | 0.36 | 0.36 |
| 7.5 minutes after Application | 0.21 | 0.21 |

TABLE 3B

Arabinogalactan

| Mean Degree of Stinging/Burning (0–6 Scale) | Base Formula A + 8% Glycolic + 5% Arabinogalactan (pH 3.8) | Base Formula A + 8% Glycolic Acid (pH 3.8) |
|---|---|---|
| Immediately after application | 0.89 | 0.47 |
| 2.5 minutes after Application | 1.0 | 0.78 |
| 5.0 minutes after Application | 0.89 | 0.63 |
| 7.5 minutes after Application | 0.63 | 0.52 |

TABLE 3C

50-HB-100

| Mean Degree of Stinging/Burning (0–6 Scale) | Base Formula A + 8% Glycolic + 5% UCON 50-HB-100 (pH 3.8) | Base Formula A + 8% Glycolic Acid (pH 3.8) |
|---|---|---|
| Immediately after application | 0.89 | 0.93 |
| 2.5 minutes after Application | 1.13 | 1.13 |
| 5.0 minutes after Application | 1.12 | 0.93 |
| 7.5 minutes after Application | 1.2 | 0.73 |

The results in Tables 3A–3C demonstrate that neither hydrocortisone nor arabinogalactan reduced the sting. In fact, addtion of 5% arabinogalactan (Table 6B) slightly enhanced the sting of the antiaging cream. The addition of EO/PO copolymer of low molecular weight also was not effective (Table 3C).

EXAMPLE 4

This example tested the effect of UCON 50-HB-5100 on delivery of glycolic acid molecules to the skin layers.

Procedure: Dermal delivery of actives was measured by the In-vitro percutaneous absorption (PCA) test. The tests were carried out using dermatomed pig skin and Bronaugh flow-through cells. 3–4 week old female dorsal pig skin, rinsed with water only was obtained from Buckshire Farms. The skins were stored at −70° C. until use. They were thawed at room temperature, shaved gently with a Norelco electric shaver, sliced to 510 um thickness using a Padgett Dermatome, punched into 18-mm discs with a cork borer, and mounted in Bronaugh diffusion cells over 37° C., pH 7.1 Hank's balanced salts buffer flowing at 5 ml/min. After 30 min equilibration, transepidermal water loss was determined using a ServoMed EP1 evaporimeter. Skin discs allowing water losses of >5 g/m2 per hr were replaced. The skin discs were dosed with 2 uL of product containing the nonlabelled active plus an insignificant weight of the active radiolabelled with 3H or 14C at about 30 microCurie/gram product. The dose was delivered via a displaced volume pipet and spread on the 9-mm diameter exposed skin surface with either a latex finger cot stretched over a cotton is tip applicator. Contact times were 6 hours, with receptor fluid being sampled at either 1- or 2-hour intervals in scintillation vials. At the end point, the skin surface was rinsed with triplicate ~1 -ml aliquots of water, the skin discs were removed from the apparatus, and blotted with ⅓ of tissue paper (Kim Wipe). The upper surface was tape-stripped 9 times with Scotch transparent tape to obtain the stratum corneum, and the epidermis was separated from the dermis with a scalpel. Analysis by liquid scintillation spectrometry included all samples necessary to account for complete balance and recovery of the radiolabelled material, including product retained on the applicator during delivery, the water-rinsed and excess removed on the tissue, tape stripped stratum corneum, epidermis, dermis (counted after NCS digestion), receptor fluid, the empty Bronaugh cells, filter papers, and rinse pipets. Theoretical applied dose was determined by subtracting the material retained on the applicator from the mean measured radioactivity of a minimum of six weighed 2-uL aliquots of the radiolabelled test product. Data were reported as percent-of-dose in tissue fractions. A p-value of ≧0.1 was considered statistically significant.

The results that were obtained are summarized in Table 4A.

TABLE 4A

| Skin Tissue | Base Formula A + 8% glycolic acid; pH = 3.8 | Base Formula A + 8% glycolic acid + 5% UCON 50-HB-5100; pH = 3.8 |
|---|---|---|
| Stratum Corneum | 2.8 | 2.5 |
| Epidermis + Dermis | 2.2 | 2.6 |
| Receptor Fluid | 1.1 | 0.9 |
| Total | 6.1 | 6.0 |

It can be seen from the result in Table 4A that the addition of 5% EO/PO copolymer did not affect the delivery of glycolic acid to different skin tissue layers.

Thus, the results of Example 2 demonstrate that the EO/PO copolymer reduced the sting caused by weak acids. Other known anti-irritants, such as hydrocortisone and arabinogalactan, did not reduce the sting caused by weak carboxylic acids (Comparative Example 3). Unlike numerous prior art approaches, the addition of EO/PO copolymer did not adversely affect the delivery of actives to skin layers (Example 4).

EXAMPLE 5

Example 5 illustrates topical compositions according to the present invention. The compositions can be processed in conventional manner. They are suitable for cosmetic use. In particular the compositions are suitable for application to aged and/or UV-damaged skin to improve the appearance and the feel thereof as well as for application to healthy skin to prevent or retard deterioration thereof.

A typical oil-in-water emulsion within the scope of the invention is as follows:

| chemical name | wt. % |
| --- | --- |
| EO/PO random copolymer | 4 |
| glycolic acid | 7 |
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| peg-40 stearate | 1 |
| peg-100 stearate | 1 |
| sorbitan stearate | 1 |
| ammonium hydroxide | to pH 4.0 |
| water DI | qs to 100% |

Another typical oil-in-water emulsion within the scope of the invention is as follows:

| chemical name | wt. % |
| --- | --- |
| EO/PO random copolymer | 5 |
| glycolic acid | 10 |
| propylene glycol | 1 |
| hydroxyethylcellulose | 0.5 |
| magnesium aluminum silicate | 0.5 |
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1.5 |
| peg-40 stearate | 1 |
| peg-100 stearate | 1 |
| sorbitan stearate | 1 |
| cetyl alcohol | 0.5 |
| ammonium hydroxide | to pH 3.8 |
| water DI | qs to 100% |

A typical water-in-oil dispersion within the scope of the invention is as follows:

| chemical name | wt. % |
| --- | --- |
| isostearyl neopentanoate | 20 |
| peg-8 caprylic/capric glycerides | 6 |
| cetyl octanoate | 17 |
| polyglyceryl-6 dioleate | 15 |
| cyclomethicone | 20 |
| glyceryl isostearate | 0.5 |
| isostearic acid | 0.5 |
| ceramide III | 0.1 |
| ppg-5-cetheth-20 | 3 |
| L-lactic acid/potassium lactate | 6 |
| hydroxycaprylic acid | 0.1 |
| water DI | 1.3 |
| EO/PO random copolymer | 10 |

The following oil-in-water emulsion within the scope of the invention is prepared:

| chemical name | wt. % |
| --- | --- |
| xanthan gum | 0.2 |
| disodium EDT | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| EO/PO random copolymer | 6 |
| glycolic acid | 3 |
| malic acid | 2 |
| lactic acid | 2 |
| triethanolamine | to pH 3.8 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of reducing skin irritation or sting caused by topical application of a weak caboxylic acid having pKa of above about 2, the method comprising topically applying a cosmetic composition comprising from 0.1 to 20 wt. % of a random ethylene oxide and propylene oxide copolymer and about 4 to 20 wt. % of a weak carboxylic acid having pKa of above about 2 in a cosmetically acceptable vehicle, wherein the pH of said composition is in the range of from 3 to 5.

2. The method of reducing skin irritation of claim 1, wherein said weak carboxylic acid is glycolic acid.

3. A method of reducing skin irritation or sting caused by topical application of a weak carboxylic acid having pKa of above about 2, the method comprising topically applying the cosmetic composition comprising:

(i) from 0.1 to 20 wt. % of a random copolymer of ethylene oxide and propylene oxide having a number average molecular weight of at least about 1,000 D and containing less than 70% propylene oxide units by weight of the copolymer;

(ii) about 1 to about 20 wt. % of a weak carboxylic acid having pKa of above about 2; and (iii) a cosmetically acceptable vehicle;
    wherein the pH of said composition is in the range of from 3 to 5.

* * * * *